United States Patent
Langer et al.

(10) Patent No.: US 11,648,381 B2
(45) Date of Patent: May 16, 2023

(54) THERMALLY CONTROLLED RESIDENCE DEVICES

(71) Applicants: Massachusetts Institute of Technology, Cambridge, MA (US); The Brigham and Women's Hospital, Inc., Boston, MA (US)

(72) Inventors: Robert S. Langer, Newton, MA (US); Carlo Giovanni Traverso, Newton, MA (US); Sahab I Babaee, Arlington, MA (US); Simo Pajovic, Mississauga (CA); Jiuyun I Shi, Chicago, IL (US)

(73) Assignees: Massachusetts Institute of Technology, Cambridge, MA (US); The Brigham and Women's Hospital, Inc., Boston, MA (US)

( * ) Notice: Subject to any disclaimer, the term of this patent is extended or adjusted under 35 U.S.C. 154(b) by 620 days.

(21) Appl. No.: 16/684,638

(22) Filed: Nov. 15, 2019

(65) Prior Publication Data

US 2020/0155821 A1    May 21, 2020

Related U.S. Application Data

(60) Provisional application No. 62/767,749, filed on Nov. 15, 2018.

(51) Int. Cl.
| | | |
|---|---|---|
| *A61M 31/00* | (2006.01) | |
| *A61M 5/142* | (2006.01) | |
| *A61L 31/16* | (2006.01) | |

(52) U.S. Cl.
CPC .......... *A61M 31/002* (2013.01); *A61L 31/16* (2013.01); *A61M 5/14276* (2013.01)

(58) Field of Classification Search
CPC .. A61M 31/002; A61M 5/14276; A61L 31/16
See application file for complete search history.

(56) References Cited

U.S. PATENT DOCUMENTS

| 4,758,436 A | 7/1988 | Caldwell et al. |
|---|---|---|
| 8,287,562 B2 | 10/2012 | Kasic, II |

(Continued)

FOREIGN PATENT DOCUMENTS

| EP | 0415671 A2 | 3/1991 |
|---|---|---|
| WO | WO 2016/178971 A1 | 11/2016 |

OTHER PUBLICATIONS

International Search Report and Written Opinion dated Mar. 10, 2020, for Application No. PCT/US2019/061628.

(Continued)

*Primary Examiner* — Robert A Wax
*Assistant Examiner* — Quanglong N Truong
(74) *Attorney, Agent, or Firm* — Wolf, Greenfield & Sacks, P.C.

(57) ABSTRACT

Residence devices for long term delivery of therapeutic compounds and/or for sensing one or more relevant parameters in vivo are disclosed. In one embodiment, a residence device may include a plurality of links interconnected by a corresponding plurality of flexible hinges to permit the residence device to be deformed into a contracted configuration and subsequently permitted to return to an expanded configuration once positioned in a desired location, such as the stomach, of a subject. In some instances, at least a portion of the interconnected links may include a first link segment, a second link segment, and a coupling that selectively connects the first link segment to the second link segment. The coupling may be configured to weaken or decouple a connection between the first link segment and the second link segment when exposed to a temperature greater than a threshold temperature to selectively weaken and/or disassemble the residence device.

23 Claims, 10 Drawing Sheets

(56) References Cited

U.S. PATENT DOCUMENTS

2017/0106099 A1   4/2017   Bellinger et al.
2018/0250226 A1   9/2018   Betser et al.

OTHER PUBLICATIONS

PCT/US2019/061628, dated Mar. 10, 2020, International Search Report and Written Opinion.
Invitation to Pay Additional Fees dated Jan. 17, 2020, for Application No. PCT/US2019/0616628.
International Preliminary Report on Patentability dated May 27, 2021, for Application No. PCT/US2019/0616628.
Babaee et al., Temperature-responsive biometamaterials for gastrointestinal applications. Science Translational Medicine. Apr. 17, 2019;11(488):13 pages. Supplementary Materials included. 26 pages total.
De Jong et al., The relationship between the ingestion of hot coffee and intraoesophageal temperature. Gut. Jan. 1972;13(1):24-30.
Liu et al., Triggerable tough hydrogels for gastric resident dosage forms. Nat Commun. Jul. 25, 2017;8(1):124.
Stuart et al. Emerging applications of stimuli-responsive polymer materials. Nat Mater. Feb. 2010;9(2):101-13. doi: 10.1038/nmat2614. Epub Jan. 22, 2010.
Traverso et al., Perspective: Special delivery for the gut. Nature. Mar. 26, 2015;519(7544):S19.
Zhang et al., A pH-responsive supramolecular polymer gel as an enteric elastomer for use in gastric devices. Nat Mater. Oct. 2015;14(10):1065-71. doi: 10.1038/nmat4355. Epub Jul. 27, 2015.

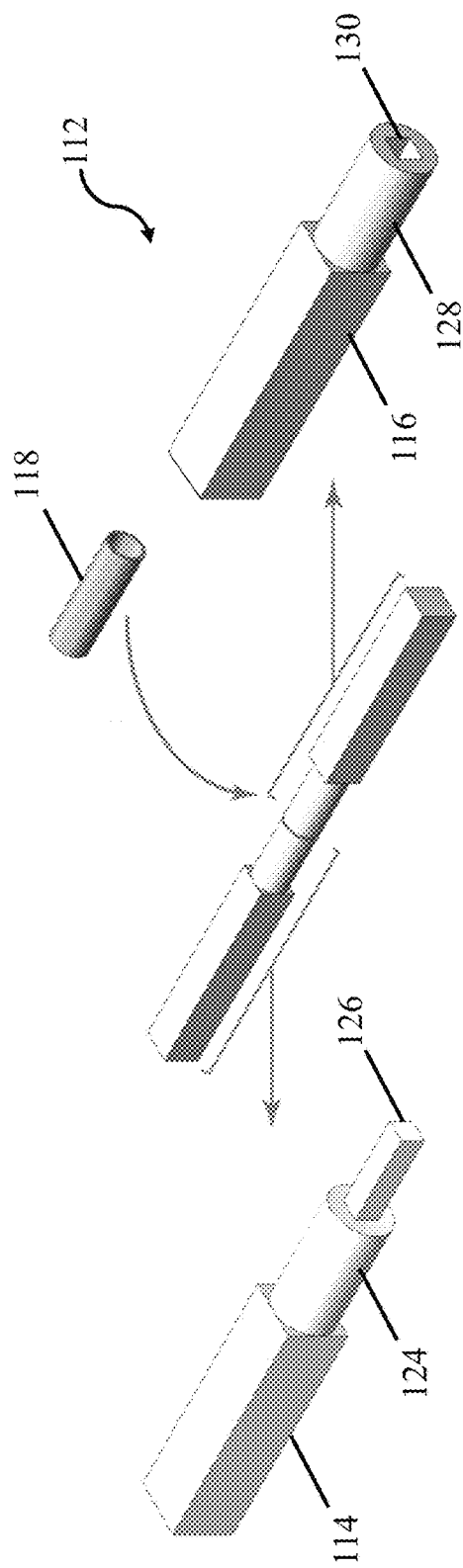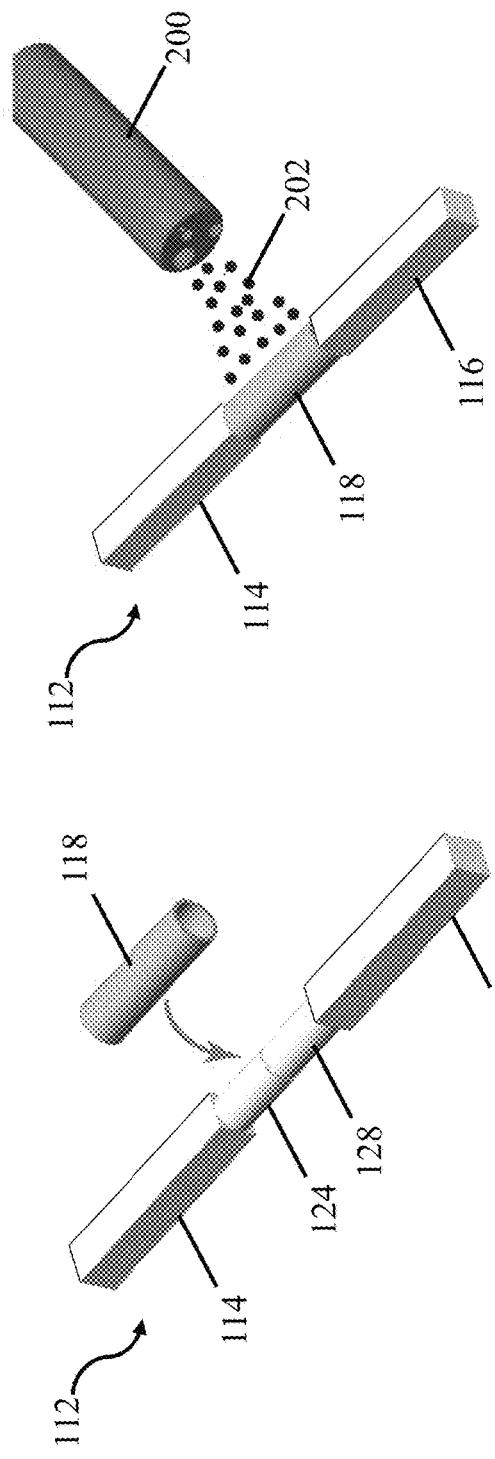
FIG. 2A
FIG. 2B
FIG. 2C

THERMALLY CONTROLLED RESIDENCE DEVICES

CROSS-REFERENCE TO RELATED APPLICATIONS

This application claims the benefit under 35 U.S.C. § 119(e) of U.S. provisional application Ser. No. 62/767,749, filed Nov. 15, 2018, the disclosure of which is incorporated by reference in its entirety.

GOVERNMENT LICENSE RIGHTS

This invention was made with Government support under EB000244 awarded by the National Institutes of Health. The Government has certain rights in the invention.

FIELD

Disclosed embodiments are related to thermally controlled residence devices.

BACKGROUND

Medication non-adherence is a major barrier to effective clinical care. For example, increasing number of medications as well as varying, complex, or prolonged dose regimens are associated with lower adherence rates by patients. Epilepsy, tuberculosis, and human immunodeficiency virus (HIV) can require complex pharmaceutical regimens for extended periods and may require personnel-intensive supervision in the form of directly-observed administration of therapy. In developed nations, adherence to long-term therapies is only 50%, and it is much lower in developing countries and in people who take multiple drugs with complex dose regimens. Current pharmacologic solutions to the adherence problem are currently limited to invasive devices and a restricted subset of low-dose pharmacologic agents.

SUMMARY

In one embodiment, a residence device includes a plurality of links and a plurality of flexible hinges. At least a portion of the plurality of links include a first link segment, a second link segment, and a coupling that selectively connects the first link segment to the second link segment. The coupling is configured to weaken or decouple a connection between the first link segment and the second link segment when exposed to a temperature greater than a threshold temperature. Each hinge pivotably connects at least two links of the plurality of links to form a flexible structure such that the residence device is reconfigurable from a first contracted configuration to a second expanded configuration.

In another embodiment, a method of using a residence device includes introducing a residence device in a first contracted configuration into the stomach of a subject, reconfiguring the residence device into a second expanded configuration once the residence device is located in the stomach, and exposing the residence device to a temperature greater than a threshold temperature to selectively weaken or disassemble at least a portion of the residence device.

In yet another embodiment, a residence device includes a plurality of links, a plurality of flexible hinges, and one or more dissolvable capsules. Each hinge is configured to pivotably connects at least two links of the plurality of links to form a flexible structure such that the residence device is reconfigurable from a first contracted configuration to a second expanded configuration. At least a portion of the residence device is disposed within the one or more dissolvable capsules in the first contracted configuration and at least a portion of the residence device extends out from the one or more dissolvable capsules. When the one or more dissolvable capsules dissolve, the residence device expands from the first contracted configuration to the second expanded configuration.

It should be appreciated that the foregoing concepts, and additional concepts discussed below, may be arranged in any suitable combination, as the present disclosure is not limited in this respect. Further, other advantages and novel features of the present disclosure will become apparent from the following detailed description of various non-limiting embodiments when considered in conjunction with the accompanying figures.

In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

BRIEF DESCRIPTION OF DRAWINGS

The accompanying drawings are not intended to be drawn to scale. In the drawings, each identical or nearly identical component that is illustrated in various figures may be represented by a like numeral. For purposes of clarity, not every component may be labeled in every drawing. In the drawings:

FIG. 2A is a schematic representation of one embodiment of a link including multiple link segments that are connected to one another via a thermally responsive coupling;

FIG. 2B is a schematic representation of the link of FIG. 2A being assembled;

FIG. 2C is a schematic representation of the link of FIG. 2A being disassembled via the application of a warm liquid to the coupling;

DETAILED DESCRIPTION

Figure 1A:
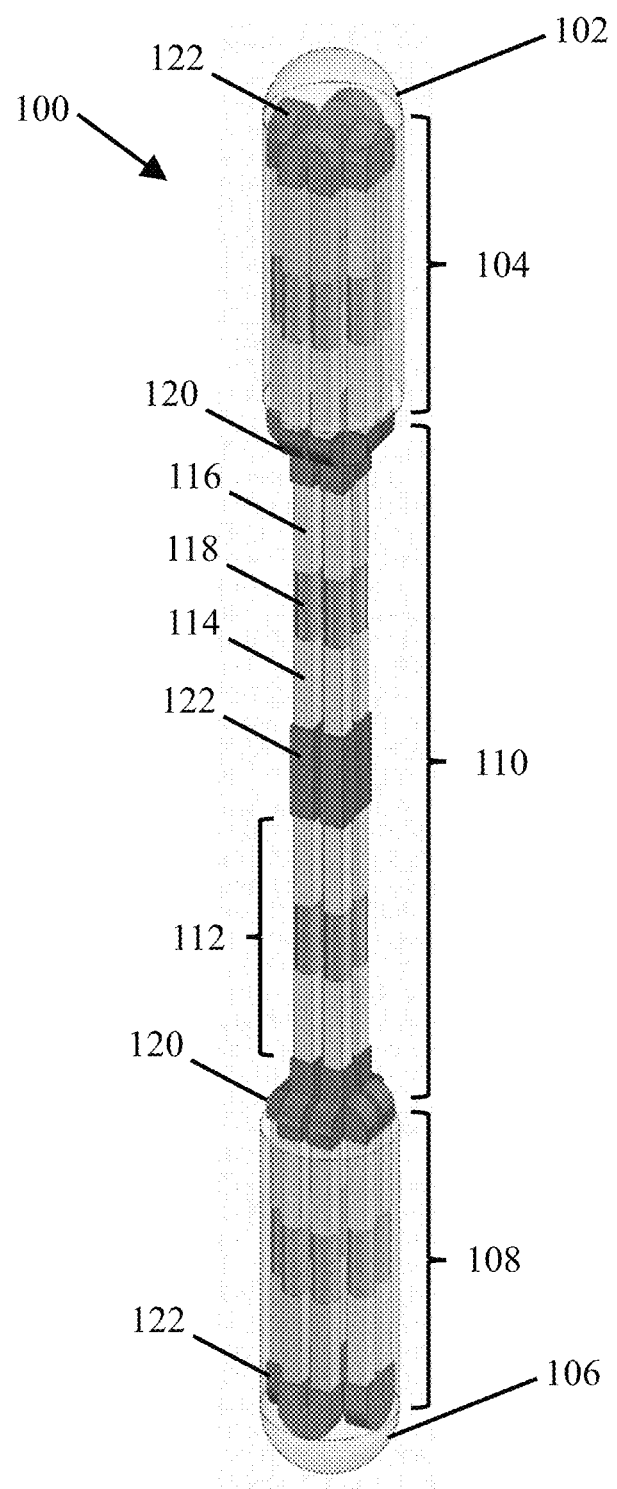
FIG. 1A is a schematic representation of one embodiment of a residence device in a contracted configuration.

As noted above, medication non-adherence is a major barrier to effective clinical care. Therefore, technologies that make it easier for patients to take their medication could have a significant societal impact. Further, gastrointestinal devices are being applied broadly across clinical indications ranging from cancer (stents, percutaneous gastrostomy tubes), bariatrics (balloons), and systems for drug delivery and long-term energy harvesting. For example, a residence device located in the gastrointestinal (GI) tract may be used to deliver a therapeutic compound and/or provide sensing capabilities over longer durations. As elaborated on further below, administering warm fluid orally results in two heat zones within a subject. Namely, an esophageal zone that experiences large temperature fluctuations and an extra-esophageal compartment, e.g. the stomach, that does not experience large temperature fluctuations with the ingestion of warm fluids were identified. The Inventors have recognized that the existence of these different temperature regions may permit the use of temperature based control for medical devices intended for use in the gastrointestinal tract.

In view of the above, the Inventors have recognized the benefits associated with a residence device that may be easily deployed, and selectively retained, in the gastrointestinal tract of a subject. Further, in some instances, it may be desirable to selectively weaken and/or disassociate the residence device while in vivo such that the residence device may pass through the gastrointestinal tract of a subject. Depending on the particular embodiment, the weakening and/or disassociation of a residence device may be triggered using one or more temperature sensitive materials and/or components. Due to the relative speed of temperature regulated material changes, the use of a temperature based material change may enable the residence device to rapidly change between a configuration that is retained within an anatomical space, such as the stomach, and a in configuration which the residence device is capable of being removed from and/or passing out of the anatomical structure as described below. In contrast, other actuation mechanisms such as light, pH, magnetic, and/or solvent responsive materials may respond more slowly. Though instances in which a material responsive to these other stimuli is used to selectively weaken and/or disassociate a residence device in place of the thermally responsive materials discussed herein are also contemplated.

In one embodiment, a residence device may be introduced into a compartment of the gastrointestinal tract, such as the stomach. However, embodiments in which the residence device is introduced into a compartment within another appropriate anatomical structure of a subject are also contemplated. The residence device may be introduced into the compartment in any appropriate fashion, including, but not limited to, ingestion of a dissolvable pill, endoscopic deployment, catheter deployment, and/or any other appropriate method of deploying a residence device into a desired location within a subject's body. During deployment, the residence device may be in a first contracted configuration. After deployment, the residence device may be reconfigured into a second expanded configuration once the device is located within the desired compartment such as the stomach of the subject. The second expanded configuration of the residence device may have at least one dimension that is larger than a corresponding dimension of the residence device in the contracted configuration. After a desired residence time within a compartment of an anatomical structure, the residence device may be exposed to a temperature that is greater than a threshold temperature. This may result in one or more portions of the residence device weakening and or disassembling from one another such that the residence device may be removed from and/or simply pass out of an opening of the compartment. For example, in a specific embodiment, a residence device located within the stomach may be large enough that it does not pass out of the pylorus until it is weakened or disassembled by application of the elevated temperature after which the device, or fragments of the device, may pass through the pylorus and subsequently through the rest of the gastrointestinal tract.

In one specific embodiment, a residence device may be constructed from a plurality of links that are connected to one another via a plurality of flexible hinges interposed between the individual links. Each of the hinges may be connected to the at least two adjacent links such that the links are pivotably connected to one another to form a flexible structure having any appropriate size and/or shape for a desired application. Thus, the residence device may be reconfigurable between a first contracted configuration and a second expanded configuration where at least one dimension of the expanded configuration is greater than a corresponding dimension of the residence device in the contracted configuration. Additionally, to permit the residence structure to be selectively weakened and/or disassembled, at least a portion of the links may be constructed using first and second link segments that are connected to one another via a coupling. The coupling may be made from an appropriate material such that when the coupling is exposed to a temperature greater than a threshold temperature, the connection between the first and second link segments may be weakened and or disassembled. Alternatively, one or more of the other components of the device, such as the flexible hinges and/or links, may be made from a thermally sensitive material to provide the desired functionality. In either case, upon exposure to temperatures is greater than a threshold temperature, a residence device may be sufficiently weakened and/or disassembled into sufficiently small fragments such that it is capable of being removed from a compartment of an anatomical structure (i.e. stomach) through surgical methods and/or by naturally passing out of the compartment during normal body functions.

In the various embodiments disclosed herein, the individual link segments of a link may be connected to one another using any appropriate coupling capable of being selectively weakened and/or removed to permit the overall selective weakening and/or disassembly of a residence device. For example, a coupling may form any appropriate connection with an adjoining link segment including, but not limited to, interference fits, adhesive bonding, interlocking features, pin connections, and/or any other type of connection capable of being selectively weakened and/or removed. In one specific embodiment, opposing end portions of two link segments may be pressed into corresponding portions of a coupling to form interference fits with the corresponding portions of the coupling they are engaged with to hold the overall link together until the coupling is subsequently removed. In another embodiment, a flexible film may be wrapped around the coupling portions of two adjacent link segments and bonded to either itself and/or the underlying link segments to form a coupling. Alternatively, the film may be permanently plastically deformed when it is wrapped onto the adjoining link segments to maintain the film in place to form a coupling. Regardless, it should be understood that a coupling may take any number of different forms and may be assembled with adjoining link segments in any appropriate manner as the disclosure is not limited to only the specifically disclosed embodiments of different couplings.

In embodiments where elevated temperatures are used to selectively weaken and/or disassemble a residence device, the elevated temperature may be applied to the residence device in any appropriate fashion. For example, in one embodiment, a warm liquid, such as water, may be sprayed onto the individual couplings of a residence device using an endoscopic device. In another embodiment, a conductive material, such as a metallic powder, may be incorporated into the couplings of a residence device such that the couplings are capable of interacting with an applied varying electromagnetic field to enable radiofrequency heating (RF heating) using a radiofrequency source located outside of a subject. In yet another embodiment, a magnetic structure, such as a magnetic material and/or structure including magnetic portions, may be heated prior to ingestion. The magnetic structure may be attracted to a magnetic material, or material attracted to magnets, included in one or more components, such as the links, couplings, and/or hinges, of a residence device. Once in contact with the residence device, the heated magnetic structure may heat at least a portion of the residence device, and in some instances substantially all of the residence device, to a temperature that is greater than the above-noted threshold temperature. In view of the foregoing, it should be understood that the disclosed residence devices may be heated using surgical applied heat sources, ingested heat sources, externally applied heat sources, and/or any other appropriate type of heat source as the disclosure is not limited in this fashion.

In the various embodiments disclosed herein, any appropriate threshold temperature for the selective weakening and/or disassembly of a residence device may be used. However, in some embodiments, the threshold temperature may be greater than normothermia within a compartment of an anatomical structure in which the residence device is deployed. For example, normothermia within the stomach and other anatomical structures is approximately 37° C. Additionally, as noted herein, drinking warm liquids does not significantly change the temperature of the fluid within the stomach. Accordingly, in some embodiments, a threshold temperature may be selected such that the couplings of a residence device are not activated upon ingestion of a warm liquid into the stomach and/or at normothermia within a given anatomical structure. Thus, a threshold temperature may be greater than or equal to 40° C., 45° C., 50° C., and/or any other appropriate temperature. Correspondingly, the threshold temperature may be less than or equal to 65° C., 60° C., 55° C., 50° C., and/or any other appropriate temperature. Combinations of the foregoing are contemplated including a threshold temperature that is between or equal to 40° C. and 65° C. Of course it should be understood that depending on the particular application, threshold temperatures both greater and less than those noted above are also contemplated as the disclosure is not limited in this fashion. Without wishing to be bound by theory, and depending on the particular materials selected for a residence device, the selective weakening and or removal of the couplings of a residence device may be due to melting, enhanced dissolution, and/or other appropriate weakening mechanism associated with a material of the couplings.

The selective weakening and/or removal of a coupling of a link of a residence device may occur over any appropriate time period after the coupling has been exposed to a predetermined stimulus such as a temperature greater than a threshold temperature. However, in some embodiments, activation times for the selective weakening and/or removal of a coupling after exposure to the predetermined stimulus may be less than or equal to 5 minutes, 1 minute, 50 seconds, 40 seconds, 30 seconds, and/or any other appropriate time period. Correspondingly, an activation time for the coupling may be greater than or equal to 1 second, 10 seconds, 20 seconds, 30 seconds, and/or any other appropriate time period. Combinations of the forgoing time periods are contemplated including, for example, an activation time to weaken and/or remove a coupling after exposure to an elevated temperature may be between or equal to 1 second and 1 minute. Of course, depending on the particular application and construction of a residence device, it should be understood that time periods greater than or less than those noted above are also contemplated as the disclosure is not limited in this fashion.

It should be understood that a residence device may have any appropriate size and/or shape in the contracted and expanded configurations for a desired application. Possible size ranges for the various components of a residence device, including residence devices deployed in the stomach of a subject, are detailed below.

In one embodiment, a size of the openings into and/or out of an anatomical structure a residence device is delivered into may place restrictions on the size of a residence device in both the contracted and expanded configurations. For example, the esophagus has a transverse dimension (i.e. diameter) between about 18 mm and 20 mm in adults and the pylorus has a transverse dimension of about 20 mm. Accordingly, residence devices delivered into the stomach, and thus passed through the esophagus the contracted configuration, may have a maximum transverse dimension in a direction perpendicular to a longitudinal axis of the residence device in the contracted configuration that is less than 20 mm, and more preferably between about 12 mm and 16 mm to easily permit the residence device to be delivered through the inner lumen of an endoscope and/or to allow the residence device to be swallowed. Correspondingly, a length of the longitudinal axis, which may correspond to the maximum dimension of the residence device in the contracted configuration, may be any appropriate length including, but not limited to, a length between about 2 cm and 30 cm, 5 cm and 30 cm, 15 cm and 25 cm, and/or any other appropriate range of longitudinal lengths as the disclosure is not limited in this fashion.

Once located in the stomach, or other appropriate anatomical structure, the residence device may expand to an expanded configuration with a minimum transverse dimension that is larger than the maximum transverse dimension of an opening out of the compartment in which the residence device is located. For example, in the embodiment in which the residence device is located in a stomach, the minimum transverse dimension of the expanded residence device may be greater than 20 mm such that it is larger than the pylorus to prevent passage of thing residence device out of the stomach through the pylorus. While any appropriate size capable of being retained in the stomach, or other anatomical structure, may be used, a minimum transverse dimension of the expanded residence device may be less than or equal to 150 mm, 100 mm, 50 mm, and/or any other appropriate dimension. Correspondingly, a minimum transverse dimension of the expanded residence device may be greater than or equal to 20 mm, 30 mm, 50 mm, 100 mm, and/or any other appropriate dimension. Combinations of the foregoing are contemplated including, for example, a minimum transverse dimension of a residence device in the expanded state may be between or equal to 30 mm and 150 mm.

It should be understood that the links included in the various residence devices disclosed herein may have any appropriate shape and/or dimension to provide a desired functionality, strength, and flexibility for a desired application while also permitting the residence device to transition between a contracted configuration and expanded configuration. That said, in some embodiments, the plurality of links included in a residence device may be an elongated structure with an approximate shape of an elongated cylinder, triangular prism, rectangular prism, or any other appropriate elongated structure having any desired cross sectional shape in a plane perpendicular to a longitudinal axis of the link oriented along a maximum dimension of the link. However, it should be understood that the links disclosed herein are not limited to only straight linear structures. Instead, in some embodiments, links with one or more curves and/or bends may also be used. Appropriate lengths for the disclosed links may be greater than or equal to 10 mm, 25 mm, 50 mm, and/or any other appropriate length. Correspondingly, a link may have a length that is less than or equal to 100 mm, 50 mm, 25 mm, and/or any other appropriate length. Combinations of the foregoing are contemplated including, for example, a link with a length that is between or equal to 10 mm and 100 mm. Additionally, links may have any appropriate transverse dimension (i.e. width or diameter) including a transverse dimension that is greater than or equal to 1 mm, 2 mm, 3 mm, and/or any other appropriate dimension. A transverse dimension of the link may also be less than or equal to 5 mm, 4 mm, 3 mm, and/or any other appropriate dimension. Thus, a link may have a transverse dimension that is between or equal to 1 mm and 5 mm or any other appropriate combination of the foregoing ranges of lengths.

While specific sizes and applications for the various components and the overall residence device are noted above, residence devices and individual components of a residence device with dimensions both greater than and less than those noted above are also contemplated as the disclosure is not limited in this fashion. For example, many of the dimensions noted above reference the sizes of anatomical structures for average adults. However, it is to be expected that the anatomical structures of children and juveniles, as well as the corresponding dimensions of a residence device used in children and juveniles, may be smaller than the dimensions noted above. Additionally, the disclosed residence devices may be used in different anatomical structures other than the stomach as well.

In addition to the overall sizing, a residence device may have any appropriate shape in either the contracted and/or expanded configurations. For example, in the contracted configuration, a residence device may have an elongated linear shape (e.g. an elongated approximately cylindrical shape), a cube, a rectangular prism, an irregular shape, and/or any other appropriate shape capable of being deployed into a desired compartment of an anatomical structure. Appropriate types of shapes of a residence device in the expanded configuration may include, but are not limited to: two dimensional structures such as a ring, square, triangle or other appropriate two dimensional structure; a three-dimensional structure such as a fenestrated spherical or semi-spherical structure, a cube, a pyramid, and/or any other appropriate three-dimensional structure capable of being formed by a plurality of interconnected links. Of course, it should be understood that while specific types of shapes are noted above, any appropriate shape capable of being deployed from a smaller contracted configuration into an expanded configuration for a desired application may be used as the disclosure is not limited to any particular shape of a residence device in either the contracted and/or expanded configurations.

It should be understood that any appropriate material may be used to form the couplings of the individual links of a residence device. For example, appropriate materials, may include, but are not limited to, polycaprolactone (PCL), thermoplastic polyurethanes (TPUs), poly(vinyl alcohol) (PVA), polylactic acid (PLA), and other appropriate materials showing temperature responsive properties capable of enabling the selective weakening and/or disassembly and/or dissolution of the associated links of a residence device.

Similar to the materials for a coupling, it should be understood that any appropriate material may be used form the individual link segments of a residence device. Appropriate materials may include, but are not limited to, polylactic acid (PLA), poly(lactic-co-glycolic acid) (PLGA), Polydimethylsiloxane (PDMS), Poly(vinyl alcohol) (PVA), Ethylene vinyl acetate (EVA), polyanhydrides, combinations of the foregoing, and/or any other appropriate polymer capable of being loaded with a therapeutic compound for subsequent extended release in vivo. Of course, embodiments in which different materials are used including polymers that are not loaded with a therapeutic compound are also contemplated.

The flexible hinges of a residence device may be made from any material that is sufficiently elastic to permit a residence device to expand from a contracted configuration to an expanded configuration. Additionally, the materials and overall construction of the flexible hinges may be selected such that the residence device may resist passing through an opening in a compartment of an anatomical structure, such as the pylorus associated with the stomach. Appropriate materials may include, but are not limited to, various polymeric and/or elastomeric materials such as thermoplastic polyurethane (TPU), silicone-based elastomers with appropriate shore hardness, and/or polydimethylsiloxane (PDMS). However, it should be understood that other appropriate materials may be used for the flexible hinges as the disclosure is not limited in this fashion.

Prior to selective weakening and/or disassembly, a residence device may have an appropriate overall flexural strength based on the design and interactions of the various components of the residence device to prevent the passage of the residence device through an opening of a compartment of an anatomical structure. For example, a flexural strength of a residence device may be selected to prevent passage through the pylorus of the stomach of a subject based on expected forces during normal usage within the stomach while still permitting food to pass through the stomach. The forces applied to a residence device may depend on the particular size, construction, and specific application. However, in some embodiments, a residence device may has sufficient flexural rigidity to prevent passage through a 2 cm opening, the average transverse dimension (e.g. diameter) of the pylorus in an adult, under a predetermined force. Depending on the particular embodiment, the predetermined force may be greater than or equal to 2 N, 3 N, and/or any other appropriate force. Correspondingly, the predetermined force may be less than or equal to 5 N, 4 N, and/or any other appropriate force. Combinations of the foregoing ranges are contemplated including, a predetermined force that is between or equal to 2 N and 5 N. Of course, embodiments in which a residence device may resist passage through an opening with a different size and/or under the application of forces both greater and less than the ranges noted above are also contemplated.

Depending on the particular embodiment, a residence device as described herein may be used to deliver one or more components to a desired location within a subject's body for an extended period of time. For example, in some embodiments, a residence device may include one or more electronic components. In one such an embodiment, the electronic components may include one or more sensors constructed to sense one or more biological parameters, biological markers, and/or any other appropriate parameter that may be sensed in vivo within the associated anatomical structure over an extended period of time. For example, within the gastrointestinal tract, an electrical signal sensor may be used to sense heart rate. In some embodiments, the sensor may be connected with one or more of a processor, non-transitory computer readable medium, a wireless transmitter (e.g. an RFID circuit or low power transmitter), and a power source (e.g. a battery, a wireless power receiver, or other appropriate power source). In such an embodiment, the various electrical components sensitive to an environment a residence device is located in may be housed in a protective housing.

In another embodiment, the various residence devices disclosed herein may be used to deliver one or more therapeutic compounds to a desired location within a subject's body for an extended period of time. In such an embodiment, one or more components of the residence device may be loaded with a therapeutic compounds. For example, the links, flexible hinges, and/or couplings of a residence device may be made from an appropriate material that may be loaded with a desired amount of a therapeutic compounds. Further, the material may be specifically configured to elute the therapeutic compound at a desired rate to provide an effective amount of the therapeutic compound over time within the desired location within the subject's body. In one such embodiment, a residence device located within a stomach of a subject may elute a therapeutic compound at a desired rate to provide an appropriate dose of the material over time to the subject.

Depending on the size and construction of a residence device, a device may contain any appropriate load of a therapeutic compound which may be delivered at any appropriate rate when positioned within a desired anatomical structure. For example, a residence device may include a load of a therapeutic compound that is greater than or equal to 1 g, 2 g, 3 g, 10 g, 20 g, 50 g, 100 g and/or any other appropriate loading. Correspondingly, the residence device may include a load of the therapeutic compound that is less than or equal to 100 g, 50 g, 20 g, 10 g, 5 g, 4 g, 3 g, and/or any other appropriate loading. Combinations of the foregoing are contemplated including a loading that is between or equal to 1 g and 5 g, 2 g and 4 g, and/or any other appropriate combination. Appropriate rates of release of a therapeutic compound from the residence device may be greater than or equal to 100 mg/day, 200 mg/day, and/or any other appropriate rate. The rate may also be less than or equal to 400 mg/day, 300 mg/day, and/or any other appropriate rate. Combinations of these rates of release of a therapeutic compound within a desired location of a subject's body are contemplated including, for example, a rate of release that is between or equal to 100 mg/day and 400 mg/day.

Therapeutic compounds for purposes of this application may correspond to any appropriate material including, but not limited to, any drug, medication, pharmaceutical preparation, contrast agent, and/or biologic such as a protein, antisense molecule, and gene therapy viral vector as the disclosure is not so limited. When a therapeutic compound is present in a particular location in an "effective amount" it means a concentration of the therapeutic compound is greater than or equal to a trace amount and is sufficient for achieving a desired purpose, such as, for example, to permit detection of the therapeutic compound in a subject for diagnostic purposes, to treat a disease or condition in a subject, and/or enhance a treatment of a disease or condition in a subject. In some embodiments, an effective amount of a particular therapeutic compound is present in an amount sufficient to reduce or alleviate one or more conditions associated with a particular condition.

In view of the above, the residence devices disclosed in the various embodiments herein may be retained in a compartment of an anatomical structure, such as a stomach, of a subject, for an extended period of time. Thus, the materials used to form the various components of a residence device may be selected to withstand the environment within the compartment of the anatomical structure for a desired residence time. For example, in embodiments in which a residence device is located within a stomach, the residence device may be subjected to gastrointestinal fluids at approximately 37° C. Accordingly, the materials selected for such a residence device may be selected to withstand exposure to the gastrointestinal fluids for the predetermined residence time while providing the desired dosing with a therapeutic compound and/or sensing of one or more parameters. Appropriate residence times may include, but are not limited to, greater than or equal to 5 days, 10 days, 15 days, 1 month, and/or any other appropriate time period. A residence time may also be less than or equal to twelve months, six months, three months, one month, and/or any other appropriate time period. Combinations of the foregoing time periods are envisioned including a residence time for a residence device that is between or equal to 5 days and 365 days.

As noted previously, the disclosed residence devices may be delivered in any appropriate fashion. For example, when ingested and/or delivered endoscopically to a stomach, at least a portion of a residence device, and in some instances an entire residence device, may be disposed within a dissolvable capsule, such as a gelatin or other appropriate capsule, that may be dissolved to deploy the residence device from the contract configuration to the expanded configuration once located in the desired location within a subject's body. In one specific embodiment, a residence device may include a plurality of links that are pivotably connected to one another by a corresponding plurality of flexible hinges such that the residence device is reconfigurable from a first contracted configuration to a second expanded configuration. One or more dissolvable capsules may include at least a portion of the residence device disposed within the one or more dissolvable capsules in the contracted configuration. Further, at least a portion of the residence device may extend out from the one or more dissolvable capsules. For example, a first portion of the residence device may be disposed within a first dissolvable capsule and a second portion of the residence device may extend out from the first dissolvable capsule towards a second dissolvable capsule. A third portion of the residence device may be disposed within the second dissolvable capsule in the contracted configuration. Thus, an overall shape of the residence device in the contracted configuration may include two portions of the residence device contained within the dissolvable capsules and another portion of the residence device extending linearly between the two capsules to form an approximate elongated cylindrical shape. Such a configuration may be desirable in that it provides an elongated structure with a longitudinal length that is substantially greater than a maximum transverse dimension of the structure in a direction perpendicular to the longitudinal length of the structure. This may be advantageous for deploying large residence devices through relatively narrow openings such as the esophagus.

While particular shapes and configurations for the contracted state of the residence device are described above, it should be understood that any appropriate shape, size, and/or arrangement of a residence device in the contracted shape may be used as the disclosure is not limited in this fashion.

The disclosed residence devices may be used for a number of different sensing and/or therapeutic applications. For example, the disclosed residence devices have the potential to house large therapeutic compound depots (in the multigram range) for the treatment of infections and other conditions where prolonged therapy may be desired. Other potential clinical applications may including nutritional modulation for bariatrics and obesity treatment. As previously noted, the disclosed residence devices may also include electrical capabilities to sense a range of signals to facilitate mobile health and the monitoring of patients suffering from chronic conditions where early detection of a signal such as bleeding or a fever could considerably enhance the capacity to intervene. The selective disassembly of the disclosed devices also enhances the simplicity and safety for facilitating the removal of the disclosed devices by breaking down a residence device into smaller fragmented portions that can naturally pass out of, or otherwise be removed from, a compartment of an anatomical structure such as the stomach.

Turning to the figures, specific non-limiting embodiments are described in further detail. It should be understood that the various systems, components, features, and methods described relative to these embodiments may be used either individually and/or in any desired combination as the disclosure is not limited to only the specific embodiments described herein.

Figures 1B, 1C:
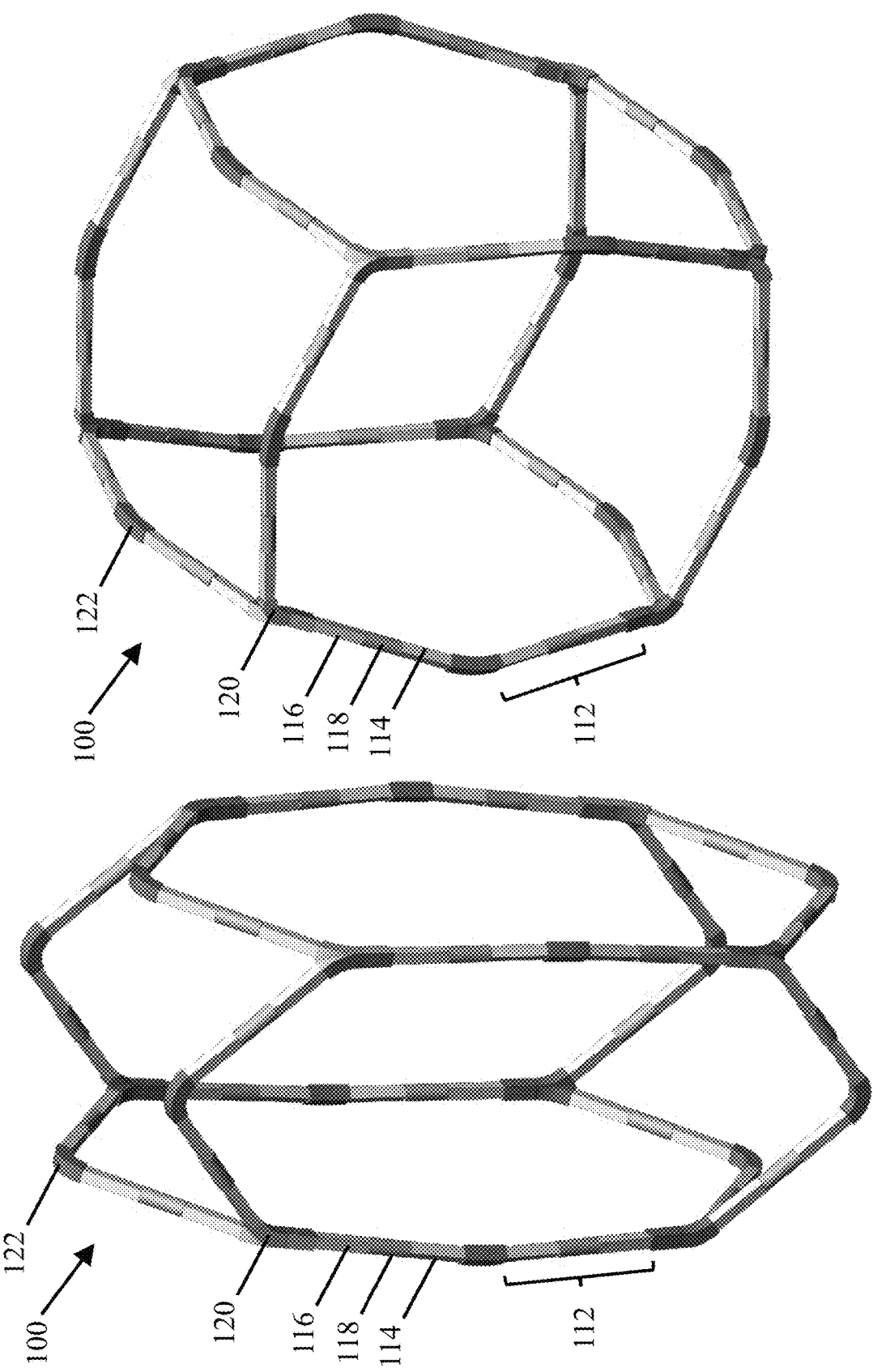
FIG. 1B is a schematic representation of the embodiment of the residence device of FIG. 1A in a partially expanded configuration.
FIG. 1C is a schematic representation of the embodiment of the residence device of FIG. 1A in an expanded configuration.

FIGS. 1A-1C depict one embodiment of a residence device 100 expanding from a first contracted configuration appropriate for insertion into a desired location within a subject's body to an expanded configuration that is appropriate for being retained within a compartment of an anatomical structure of the subject. In the depicted embodiment, the residence device is constructed from a plurality of links 112 that are interconnected by a plurality of flexible hinges 120 and/or 122 disposed between adjacent links. The flexible hinges and associated links may be connected to each other in any appropriate manner including, for example, adhesives, interference fits, mechanical interlocking features, plastic welding, and other appropriate types of connections. Depending on the specific shape of the residence device, the flexible hinges rotatably connect either two adjacent links to one another as illustrated by the flexible hinges 122 and/or the flexible hinges may rotatably connect three or more adjacent links as illustrated by the flexible hinges 120. By using combinations of these flexible hinges and interconnected links, a residence device may have various complex two-dimensional or three-dimensional structures in the expanded configuration.

As illustrated in FIG. 1A, the residence device 100 may be deformed into a contracted configuration for insertion into a compartment of an anatomical structure such as the stomach. In the depicted embodiment, a first portion 104 of the residence device is disposed within a dissolvable capsule 102. A plurality of links 112 and flexible hinges 122 connected to two adjacent links are included in this first portion of the residence device. The flexible hinges within this first portion have been deformed such that the corresponding links are located proximate to and are oriented in parallel with one another and a longitudinal axis of the residence device. Portions of the links extending out from the capsule are connected with flexible hinges 120 that interconnect three adjacent links and form corresponding corners of the resulting expanded residence device. A second portion 108 of the residence device is disposed in a second dissolvable capsule 106 located on an opposing end portion of the residence device relative to the first dissolvable capsule and corresponding first portion of the residence device. The second portion of the residence device may be formed into a contracted configuration similar to that described above regarding the first portion. Additionally, a third portion of the residence device may extend between the first and second capsules. In the depicted embodiment, the third portion of the residence device corresponds to a plurality of links that are located proximate to, and oriented parallel with, one another. The links in this third portion of the contracted residence device may also be oriented parallel to a longitudinal axis of the residence device in the contracted configuration. The resulting structure of the residence device in this contracted configuration is an elongated structure with a longitudinal length that is substantially greater than a maximum transverse dimension of the structure in a direction perpendicular to the longitudinal length of the structure. Further, as illustrated in figure, each of the links in the contracted configuration may be oriented parallel to the longitudinal axis of the residence device. However, embodiments in which the residence device is configured into a different contracted configuration and/or in which one or more of the links are not parallel to the longitudinal axis of the device are also contemplated as the disclosure is not limited to any particular shape and/or size of a residence device in a contracted configuration.

FIGS. 1B and 1C illustrate the residence device 100 expanding from the initial contracted configuration shown in FIG. 1A to an expanded configuration after the dissolvable capsules have been dissolved. As shown in the figures, the flexible hinges 120 and 122 are sufficiently resilient such that they urge the residence device to open to the expanded configuration shown in FIG. 1C. The overall construction of the individual links 122 and hinges, i.e. materials, cross-sections, lengths, overall device shape, and other appropriate parameters, may be selected to provide a desired rigidity of the overall structure. Specifically, the rigidity of the residence device in the expanded configuration may be sufficient to resist the forces expected to be applied to the residence device when deployment to maintain a minimum overall dimension of the residence device to prevent passage of the residence device out of a compartment the residence device is located in. For example, in one embodiment, the residence device may be configured to maintain an overall minimum dimension that is sufficient to prevent passage of the residence device through a subject's pylorus to retain the residence device in the subject's stomach.

As described previously, at least a portion, and in some embodiments all, of the links of a residence device may include a first link segment 114 that is connected to a second link segment 116, see FIGS. 1A-1C. One embodiment of the construction of a link and its use is best shown in FIGS. 2A-2C. In the depicted embodiment, a link includes a first link segment that includes a first coupling portion 124. The second link segment may include a corresponding second coupling portion 128. In the depicted embodiment, the first and second coupling portions are sized and shaped to form an interference fit with the corresponding coupling 118. For example, the first and second coupling portions of the first and second link segments may be press fit into opposing ends of the coupling to form an integrated link with the coupling portions of the link segments disposed within the coupling and the first and second link segments extending outward away from the coupling. Alternatively, the coupling may be a flexible film that is wrapped around the abutting first and second coupling portions. As shown in FIG. 2C, an elevated temperature may be applied to a coupling of a link to weaken and/or disassemble the first and second segments from one another. For instance, the figure depicts the use of an endoscopic device 200 used to spray a warm liquid 202 with an elevated temperature, such as warm water, onto the coupling, though other methods of raising the temperature of the coupling or other component of a residence device are also contemplated as described above.

In some instances, the first and second link segments 114 and 116 may include interlocking features 126 and 130 to aid in the assembly and/or connection of the link segments. For example, the figures illustrate the use of a rectangular prism extending longitudinally outward from the first coupling portion of the first link segment with a size and shape that fits into a correspondingly sized and shaped blind hole formed in the second coupling portion of the second link segment. It should be understood that other interlocking and/or keyed features may be used. Additionally, embodiments in which interlocking and/or keyed features are not used are also contemplated.

Figure 3:
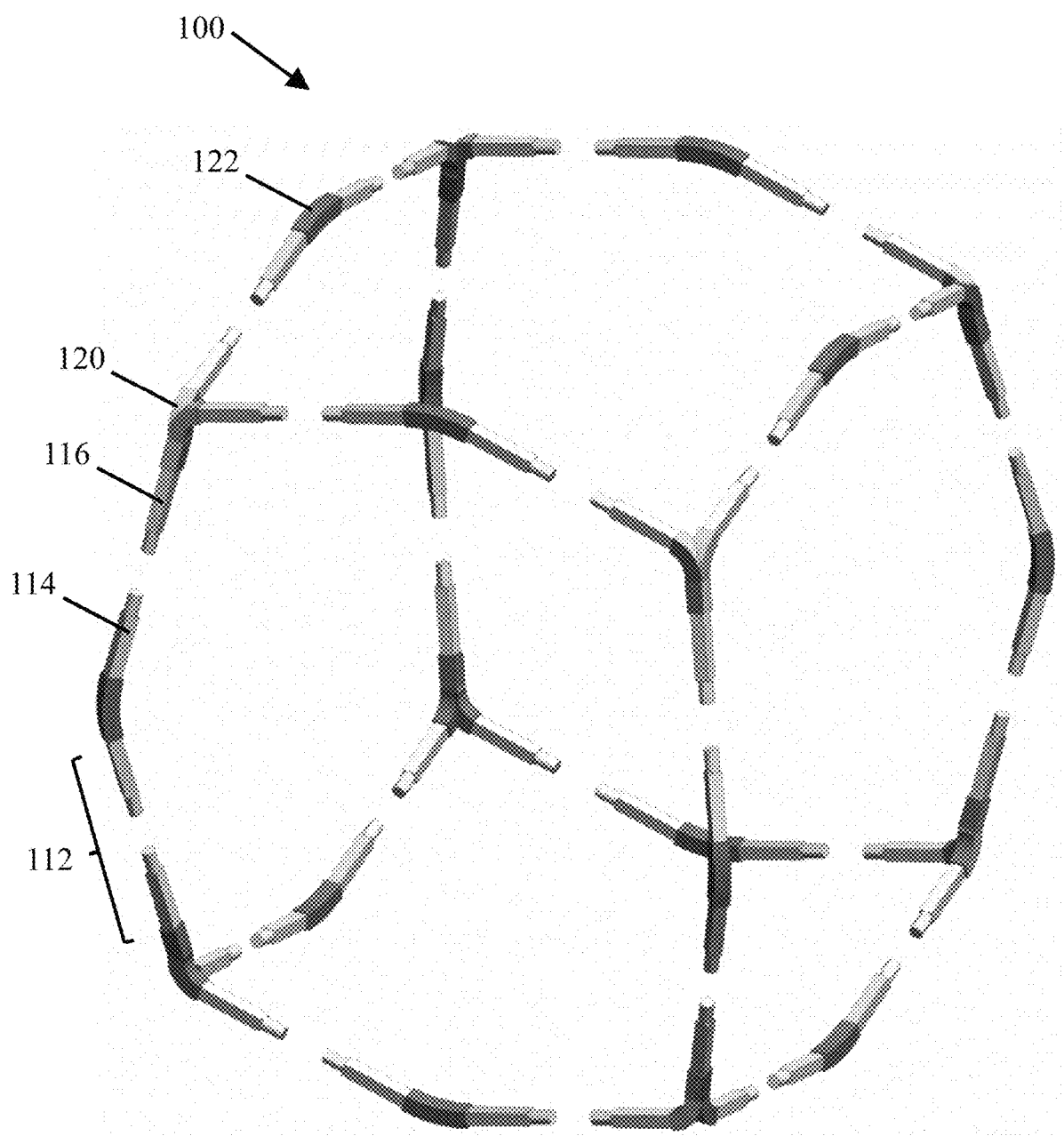
FIG. 3 is a schematic representation of one embodiment of a residence device with the couplings removed and the residence device disassembled into smaller fragments.

FIG. 3 illustrates an embodiment of a residence device 100 where the couplings have been selectively removed. As shown in the figure, the various links 112 have been disassembled into the corresponding separate first and second link segments 114 and 116. The link segments from separate links are attached to associated flexible hinges 120 and 122 which may remain attached to one another to form various fragmented portions of the residence device. These fragmented portions of the residence device may have an appropriate dimension for either surgical extraction of the fragmented portions, or more preferably, in some embodiments, the fragmented portions may have a maximum dimension that is less than a transverse dimension of an opening from a compartment of an anatomical structure such that the fragmented portions may naturally pass out of the compartment. For example, the fragmented portions may have a maximum dimension that is less than a transverse dimension of the pylorus of a subject's stomach so that the fragmented portions may pass through the gastrointestinal tract of the subject.

While the above embodiment illustrates links that are fully disassembled with the associated couplings completely removed, it should be understood that the current disclosure is not limited to only embodiments in which the couplings are completely removed. For example, embodiments in which the couplings are simply weakened to a point that the residence device is able to collapse and exit through an opening of a compartment of anatomical structure are also contemplated. Alternatively, the couplings may be sufficiently weakened such that natural forces applied to the device in a deployed configuration, such as stomach contractions, may break the weakened residence device down into the desired fragmented portions.

Figure 4:
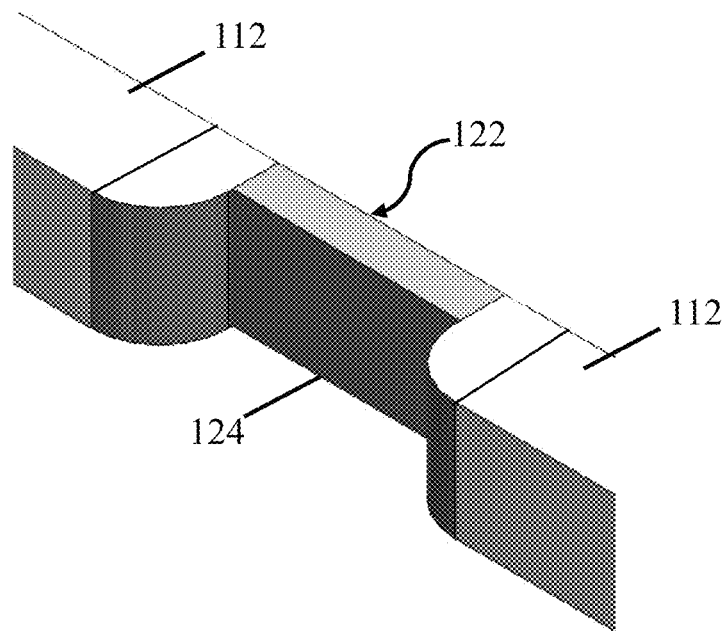
FIG. 4 is a schematic representation of one embodiment of an elastic hinge disposed between two links.
Figure 5:
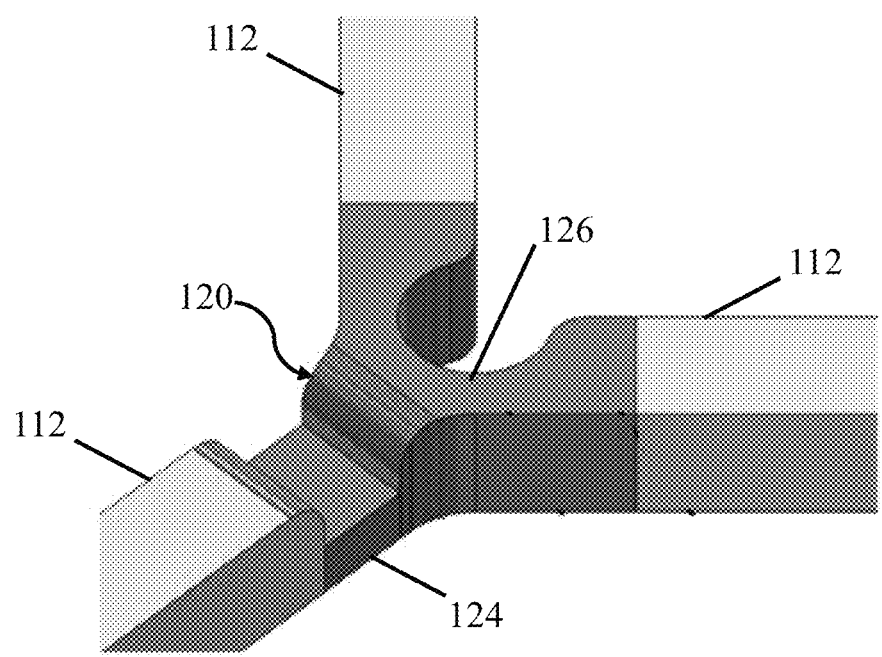
FIG. 5 is a schematic representation of one embodiment of an elastic hinge disposed between three links.

FIGS. 4 and 5 illustrate two possible embodiments of flexible hinges 120 and 122 which may be used to rotatably connect either two links 112 or three links 112 to one another at a desired location respectively. While any appropriate construction and material may be used to provide a flexible hinge, as depicted in the figures, in some embodiments, a hinge may include the use of portions with a reduced cross-sectional area 124 as compared to surrounding portions of the hinge and/or cutouts 126 to create portions of reduced cross sectional area in a hinge. In some embodiments, these regions of reduced cross sectional area may function as living hinges in one or more portions of the flexible hinge to permit rotation of the attached links relative to one another in one or more desired directions. Of course, it should be understood that other appropriate flexible hinges may also be used as the disclosure is not limited to any particular flexible hinge construction.

Example: In Vivo Evaluation of Heat Dissipation in the Upper Gastrointestinal Tract The temperature in the esophagus and stomach during administration of warm water was measured in a large animal model (three Yorkshire pigs). After anesthesia, an endoscopic overtube (US Endoscopy) was placed into the esophagus under endoscopic visual guidance during esophageal intubation. Next, a temperature setup, made of an array of 16 K-type thermocouple probes, was inserted through the overtube into the esophagus and stomach, and the overtube was then removed. The thermocouples were spaced 5-cm apart along a length of the esophagus and within the stomach. When the correct placement was confirmed by radiographs (the position of all the probes was matched across all the experiments), the overtube was withdrawn such that the distal tip was at the proximal esophagus. Then, the pigs were secured in the seated position to mimic the orientation of the human GI tract while drinking.

A range of volumes of 55° C. warm water (V=10, 20, 50, 100, 200, and 250 ml) were administered over 10 s periods (steady-state flow rate), and the temperature was recorded using the data loggers for all the probes. Each measurement was repeated three times in three different pigs with 2-min intervals between the tests to ensure that the body temperature recovered to its initial value (35° to 37° C.) before beginning a new test. For the high volumes of input water (V=100, 200, and 250 ml), the water was evacuated from the stomach using vacuum suction after every measurement. The pouring period was 10 s for all the volumes except for V=10 and 20 ml, where the entire volume of water was poured quickly to mimic a single gulp.

The measured temperature data confirmed that temperature could be controlled in the esophagus and in the proximal stomach using high volumes of warm water (100, 200, 250 mL). Low volumes of warm water (10, 20 mL) in the range of a single gulp manifested in minimal temperature changes supporting that accidental actuation of thermo-responsive components through daily consumption of hot beverages is unlikely. Interestingly, the temperature change was negligible in the bulk of the stomach regardless of the volume ingested confirming the existence of two temperature zones where the esophagus shows changes in temperature due to the ingestion of warm fluids and ex-esophageal structures such as the stomach show little to no changes in temperature due to the ingestion of warm fluids.

Example: Device Manufacture and Testing Procedures

A highly-foldable residence device similar to that shown in FIGS. 1A-1C was designed using three components: semi-rigid links to carry therapeutic agents; elastomeric hinges to provide flexibility of the dosage form; and thermo-responsive couplings for disassembly and safe passage of the residence device from the stomach of a subject.

The residence device was made of 24 links of 50 mm length with 2.6×2.6 mm square cross-sections, which were joined using elastic hinges. Each arm was made of two segments mechanically mated each with a 25 mm length and connected using thermo-responsive couplings. The elastic hinges enabled the residence device to be deformed to a shape and size that could be safely passed through the esophagus such that it was delivered to and expanded in the stomach. After deployment, the residence device adopted a fenestrated spherical shape, see FIG. 1C. As detailed below, the thermo-responsive couplings were constructed such that they could be weakened by endoscopically spraying with warm water (T=55° C.) but remain stable in the acidic gastric environment. During construction and use, the thermally responsive couplings were: (i) wrapped around the link segments to provide stability and integrity of the residence device, and (ii) weakened upon spraying with 55° C. water causing the residence device to be disintegrated into small fragments in a predictable manner that were capable of exiting the stomach and passing through the intestine without obstruction or perforation of the bowels.

The residence device was fabricated from three constitutive materials: (i) injection molded PCL (molecular weight—40 kDa, Capa™ 6400, Perstorp) used for the links, (ii) thermoplastic polyurethane (Elastollan® 1185A from BASF) used for the elastomeric hinges, and (iii) thermo-responsive polymeric couplings made from a 1:2 (by weight) mixture of low molecular weight PCL (molecular weight—10 kDa, Sigma) and polycarbonate based thermoplastic polyurethane (PC-3575A, Lubrizol). The thermo-responsive couplings were provided in the form of a thin film that was cut to shape. The couplings were then wrapped around the coupling portions of the assembled link segments of each link. To hold the thin films in place, the thin film was connected to itself using dichloromethane after wrapping around the coupling portion of the associated link.

The above described residence device was deployed in the gastric cavity of a pig model using endoscopic deployment and testing was conducted as described further below. After 1 week of retention the animal was fasted overnight. The gastric cavity was accessed endoscopically and the thermo-responsive couplings were sprayed with 200 ml of 55° C. warm water. Disruption of the thermos-responsive couplings was observed in vivo.

The above described residence device may be used as a platform for housing large depots of a therapeutic compound for extended release over the course of several weeks. Importantly, due to the unique response of the stomach to warm fluids, the structure can be triggered by local administration of warm liquids without normal ingestion of warm liquids and/or food triggering the residence device. Interestingly, the reconfigurable behavior and foldability of the proposed metamaterials offer two advantages: compaction under compression accompanied with significant volume reduction to facilitate the safe delivery of metamaterials and large depots of therapeutic compounds through narrow orifices in the digestive system such as the esophagus; and expansion inside the stomach to achieve prolonged retention and prevent exiting through the pylorus while allowing the passage of food.

Example: Therapeutic Compound Formulation and Release Rate

The links of the tested residence devices were loaded with separate dosages of two drugs: (i) carbamazepine (CAR), a drug commonly used to treat epilepsy, and (ii) moxifloxacin (MOX), an antibiotic. Poor adherence to treatment protocols for these drugs, estimated from 50 to 70%, is a major cause of treatment failure resulting in poorly controlled epilepsy and bacterial infections respectively. The average daily dose for these drugs is between 200 mg to 400 mg. Thus, a high-capacity residence device is desired for their extended delivery.

Various polymeric formulations of CAR and MOX were synthesized and studied to evaluate the effect of changing drug loading, general material composition, additives, and the application of a polymeric coating on drug release. Due to the limited solubility of CAR in simulated gastric fluid (SGF), 5% (w/v) Tween 20 was added to the release medium. To perform the release study, drug-polymer matrices (~1 cm in length) were incubated with 50 ml of the respective release medium in a 37° C. incubator shaker at 50 rpm. At various times, 1 ml of the release medium was collected and stored at −20° C. until further analysis. The remaining medium was discarded, and the arms were incubated with fresh medium. For measuring drug concentrations in the release medium, all specimens (beam-like arms) were thawed, centrifuged at 1500 g for 10 min, and analyzed using high-performance liquid chromatography (HPLC).

Figure 6:
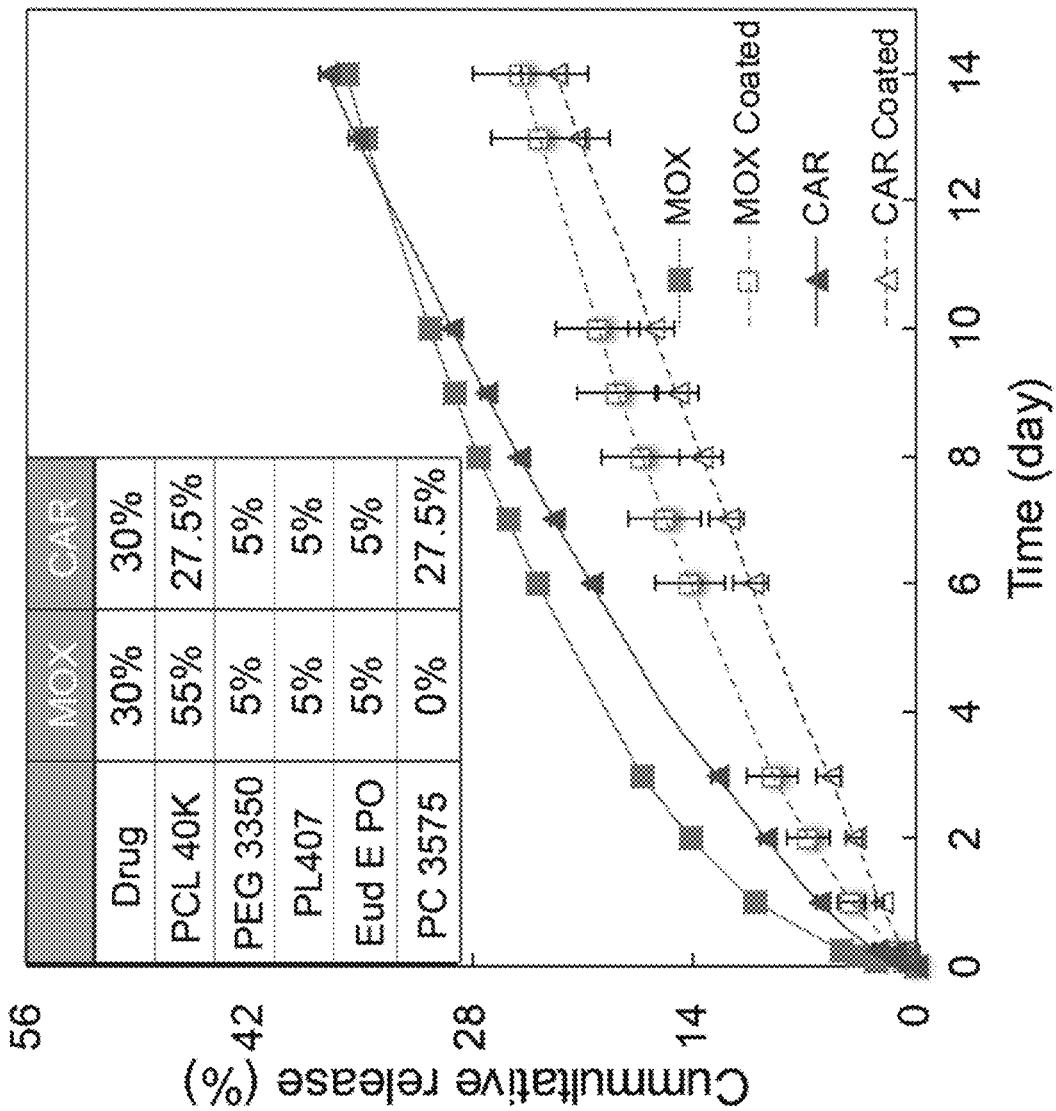
FIG. 6 is a graph of in vitro release of therapeutic compounds from coated and uncoated moxifloxacin and carbamazepine loaded arms incubated in 37° C. simulated gastric fluid for 14 days.

Depending on the drug used, the links had excipients and elasticizers added to enhance the drug release and mechanical properties, respectively. For both moxifloxacin (Alchem Pharmtech, Inc) and carbamazepine (Ark Pharm, Inc), poly (ethylene glycol) (PEG) (molecular weight—3350 Da, Spectrum Corp.), Kolliphor® P 407 (BASF), and EUDRAGIT® E PO (Evonik) were used as excipients. For carbamazepine, Carbothane™ TPU PC3575A was used as an elasticizer. For X-ray visualization, 15% weight ratio of $BaSO_4$ was added. Various polymeric formulations were investigated for controlled release of the drugs. The in vitro drug release was also investigated by changing drug loading and the composition of excipients, as well as application of polymeric coating (using a solution of 5.4% PCL (w/v) and 0.6% EUDRAGIT® E PO (w/v) in acetone). For example, the fraction of moxifloxacin released over 2 weeks doubled (and total amount of moxifloxacin release nearly tripled) upon increasing moxifloxacin loading from 35% w/w to 50% w/w. Drug release may be accelerated further by the inclusion of a surfactant such as PluronicP407. Inclusion of hydrophilic excipients had similar effects on the release of carbamazepine. Release of carbamazepine increased by greater than 3-fold due to the addition of water soluble polymers such as PEG 3350 and Kolliphor® P 407 to the polymer matrix. This increase in drug release could be attributed to a higher initial burst as well as an overall increase in the rate of drug release during the zero-order phase. The initial burst could be suppressed by coating the polymer matrix with a thin layer of poly(caprolactone) and EPO (EUDRAGIT®). A comparison of coated and uncoated links loaded with CAR and MOX over a period of 14 days is shown in FIG. 6.

In view of the above, there is a wide range of formulations for moxifloxacin and carbamazepine where the release rate may be modified to achieve the desirable pharmacokinetics for drug delivery using a residence device.

Example: In Vivo Drug Stability

Given that the tested residence device is designed to reside in the stomach for an extended period, the drug stability was analyzed in simulated gastric fluid (0.2% w/v sodium chloride, and 0.7% w/v hydrochloric acid, adjusted to pH-1.2; referred to as SGF). Moxifloxacin was dissolved in SGF and placed at 37° C. At various times, part of the solution was aliquoted and stored at about −20° C. until further analysis. For carbamazepine, the drug was first dissolved in methanol and then diluted in SGF (at least 100-fold). At various times, part of the solution was collected and stored at −20° C. On completion of the study, drug concentration in the various aliquots was measured using high performance liquid chromatography-ultraviolet (HPLC-UV) analysis (High Performance Liquid Chromatography).

Figure 7:
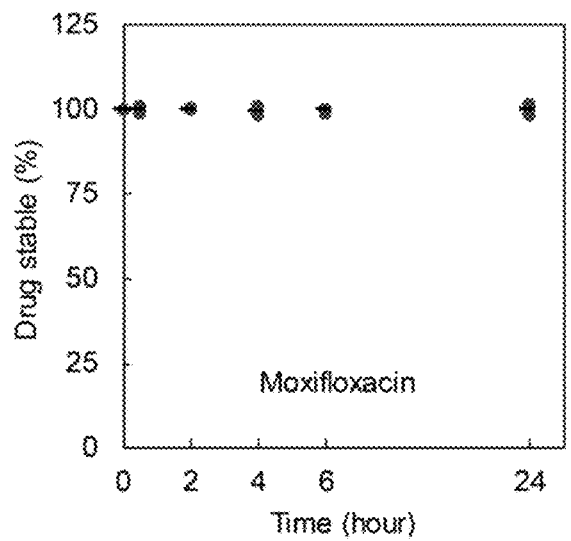
FIG. 7 is a graph of drug stability in simulated gastric fluid versus time for moxifloxacin.
Figure 8:
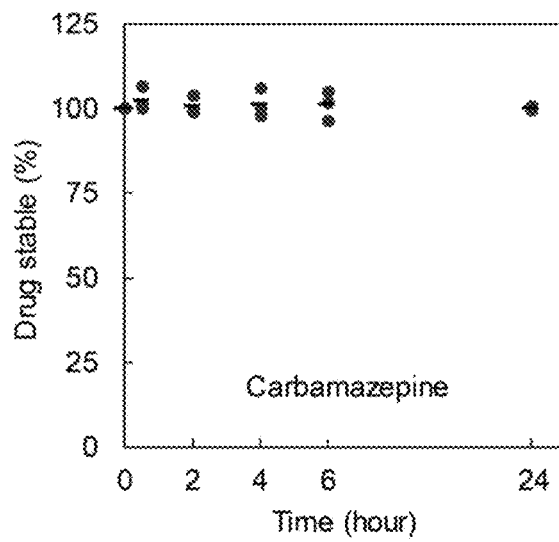
FIG. 8 is a graph of drug stability in simulated gastric fluid versus time for carbamazepine.
Figure 9:
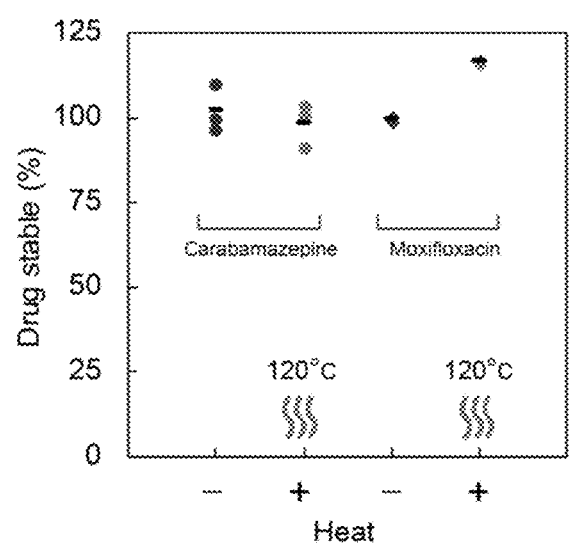
FIG. 9 is a graph of drug stability for elevated temperatures for moxifloxacin and carbamazepine.

As shown in FIGS. 7 and 8, both moxifloxacin and carbamazepine were stable in SGF for the 24 hour duration of the experiments. Additionally, drug stability was evaluated for an elevated temperature of 120° C. which may be reached during the manufacturing of the dosage form. As shown in FIG. 9, no appreciable drug degradation was observed due to exposure to the noted temperature.

Example: In Vivo Gastric Retention and Prolonged Drug Delivery

To evaluate the ability of residence devices loaded with the selected carbamazepine formulation to achieve gastric retention, the above described residence device was administered to a large animal model (three 35 to 50 kg Yorkshire pigs for each drug). Following overnight fasting and sedation of the animals, an overtube (US Endoscopy), with endoscopic guidance, was placed into the stomach to facilitate direct gastric delivery of the residence device. A residence devices folded into a cylindrical shape of length 20 cm and diameter of 12 mm (see the folded configuration in FIG. 1A) was administered via the overtube into the stomach of each pig, and the overtube was then removed. Gastric residence and in vivo drug release experiments were performed with dosage forms that did not contain thermo-responsive couplings for safety evaluation. Serial radiographs were performed immediately afterwards and every 48-72 hours to monitor the integrity and transit of the devices as well as any radiographic evidence of bowel obstruction. In addition, animals were monitored clinically at least twice a day for any evidence of morbidity, including lethargy, inappetence, decreased fecal output, abdominal distension and vomiting. No adverse events, obstruction of pylorus or limitation in passage of food or liquid were observed during the studies associated with these dosage forms. Endoscopic evaluation of the stomach over the course of the study was performed to further explore the stomach and ensure the absence of any ulceration or injury. Blood samples were taken at the following time points, 0 min (before administration of the dosage form), 5 min, 15 min, 30 min, 2 hours, 6 hours, daily for a minimum of 5 days, and then three times for the second week from peripheral veins under sedation.

Figure 10:
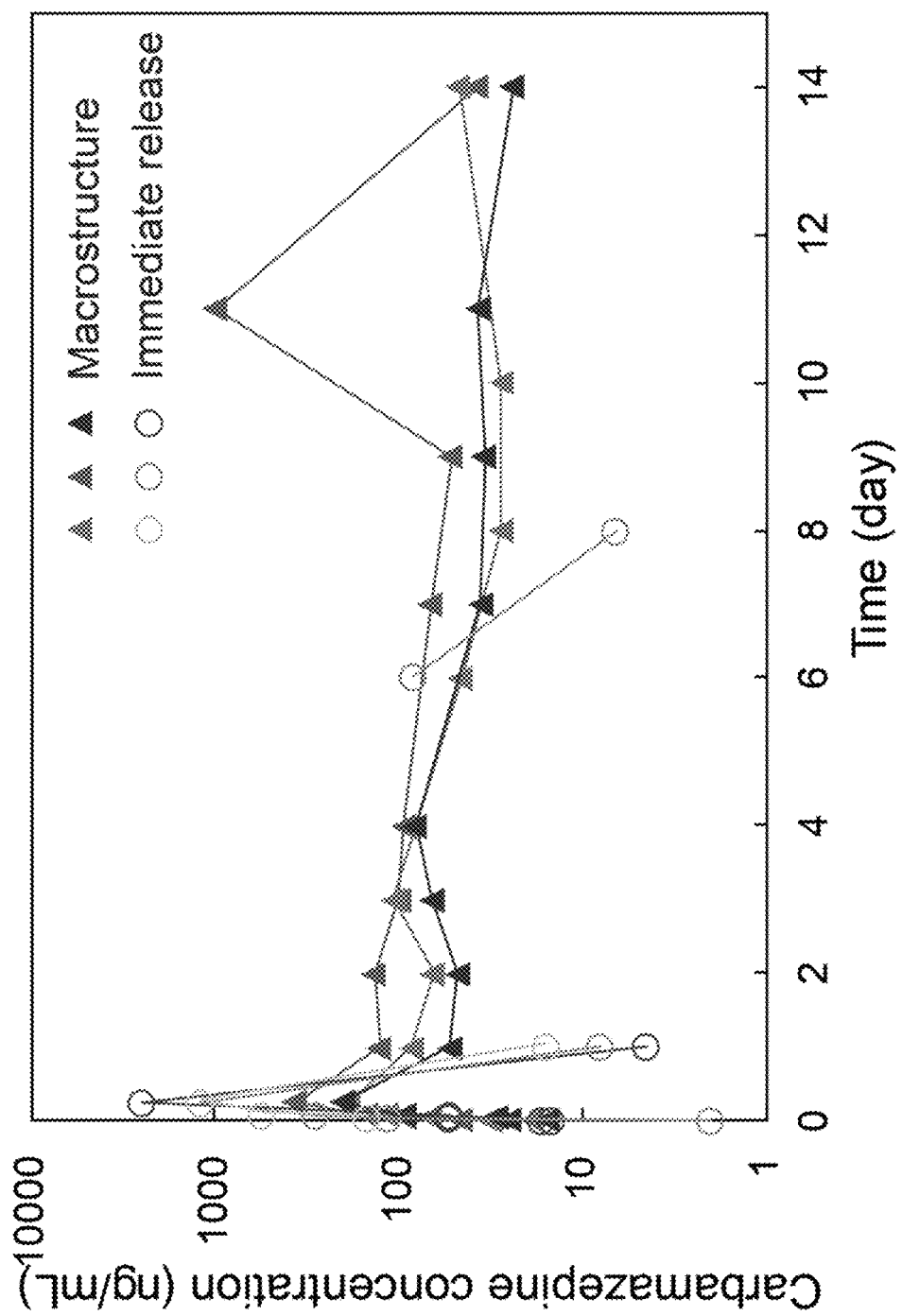
FIG. 10 is a graph comparing carbamazepine concentration versus time for doses delivered using the disclosed residence devices as compared to concentration for an immediate release treatment.

One hundred microliters of each blood sample was spiked with 200 μl of 250 ng/mL internal standard (imipramine for carbamazepine) with acetonitrile added to elicit protein precipitation. Samples were vortexed, sonicated, and centrifuged prior to being pipetted into a well plate containing 200 μl of nanopure water. Finally, the samples were injected into an Ultra Performance Liquid Chromatography tandem mass spectrometry (UPLC-MS/MS) for analysis. Carbamazepine concentration versus time in the pig models over the 14 day residence time is presented in FIG. 10. An initial spike in concentration was observed in the first day followed by relatively uniform concentrations over the duration of testing. In contrast, immediate release compositions administered to pig models showed an immediate spike in concentration followed by a decrease in concentration to an amount less than the average concentration observed with the residence devices. Thus, following a single administration event with the disclosed residence devices carbamazepine was delivered for up to 14 days while providing a lower maximum concentration and an enhanced area under the curve attributable to the sustained release of the drug as compared to immediate release formulations.

Example: In Vivo Disassembly of Residence Device

A residence device was deployed in the stomach of a pig model as detailed above. After 1 week of retention the animal was fasted overnight. The gastric cavity was accessed endoscopically and thermos-responsive linkages sprayed with 200 ml 55° C. warm water. Serial images were collected to confirm the selective weakening of the thermos-responsive couplings and subsequent fragmentation of the residence device into smaller separated portions.

Example: Mechanical Characterization

Figures 11, 12:
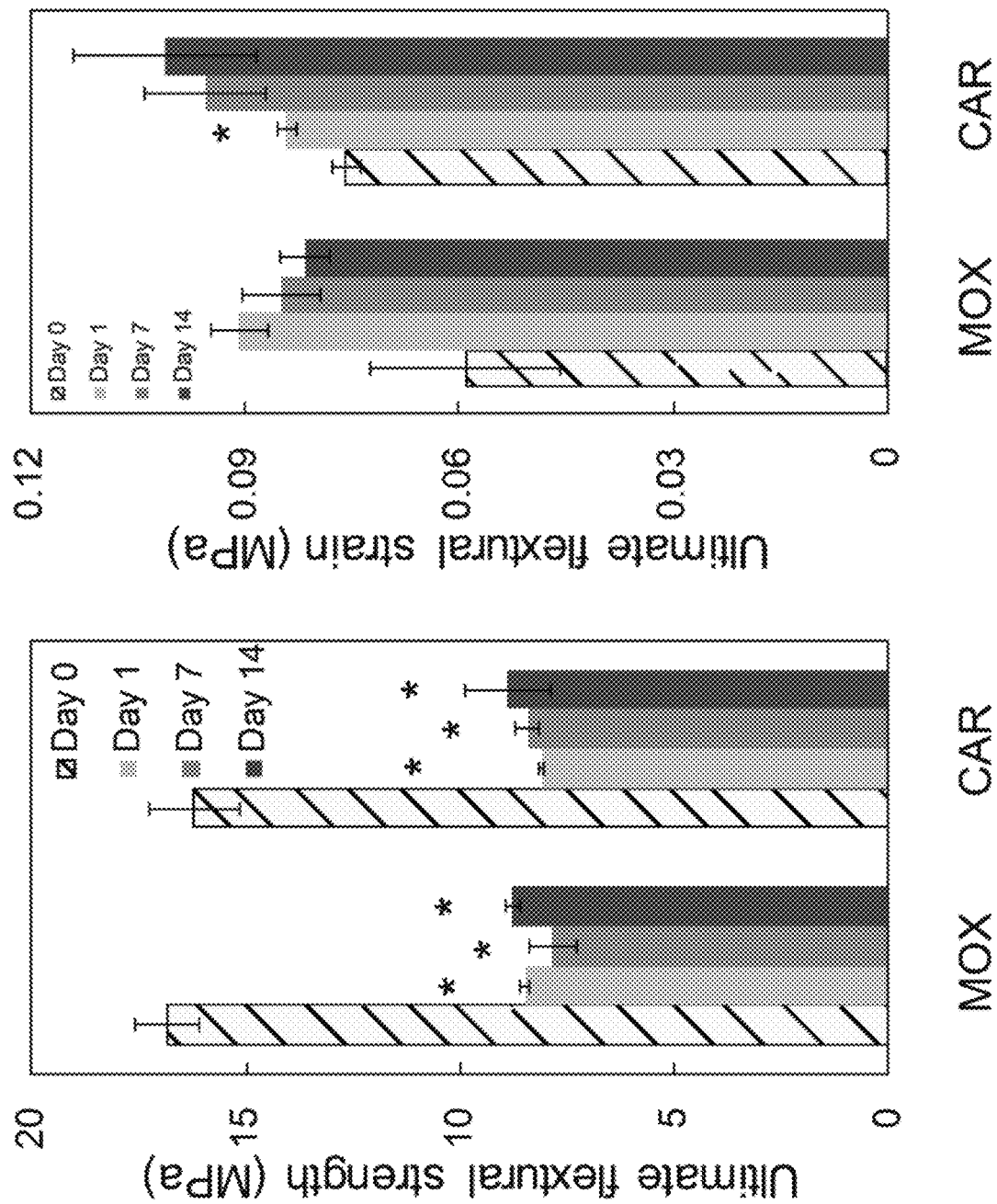
FIG. 11 is a graph of ultimate flexure strength of moxifloxacin and carbamazepine loaded arms incubated in 37° C. simulated gastric fluid for times varying up to 14 days.
FIG. 12 is a graph of ultimate flexure strain of moxifloxacin and carbamazepine loaded arms incubated in 37° C. simulated gastric fluid for times varying up to 14 days.

To achieve long-term gastric residence, drug-loaded arms with different formulations may retain sufficient mechanical strength and flexibility to withstand gastric contractions. A comprehensive mechanical characterization of drug-polymer arms using three-point bending assay was conducted. The specimens (i.e., drug-loaded arms) were placed in 50 mL of simulated gastric fluid (SGF) and left for 1, 7, and 14 days in a 37° C. incubator shaker at 100 RPM. The bending test was then conducted for each time point as well as a day 0 control. The data is presented in FIG. 11 (ultimate flexural strength) and FIG. 12 (corresponding flexural strain) for both drugs. Note that it is desirable for the drug loaded links to be flexible enough over time to endure gastric forces and avoid breaking. This was achieved by including an elasticizer, polycarbonate based thermoplastic polyurethane (PC-3575A, Lubrizol), to the formulations. In one instance, a relatively brittle formulation was used (ultimate flexural strain ~0.012 with no elasticizer included). The brittle formulation readily fractured into small pieces in the stomach after delivery even though the material exhibited high strength (ultimate flexural strength greater than 35 MPa). Moxifloxacin formulations naturally exhibited a ductile response (ultimate flexural strain greater than 0.06) that guaranteed high durability of the drug-polymer arms for prolonged gastric retention.

Figure 14:
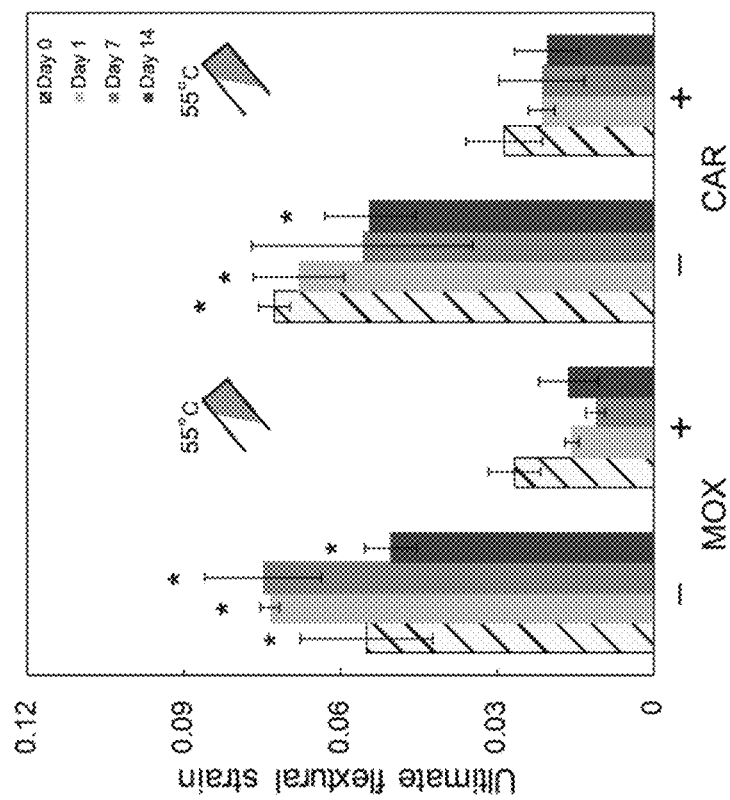
FIG. 14 is a graph of ultimate flexure strain of moxifloxacin and carbamazepine loaded arms that have been incubated in 37° C. simulated gastric fluid for times varying up to 14 days prior to and after exposure to fluid with a temperature of 55° C.
Figure 13:
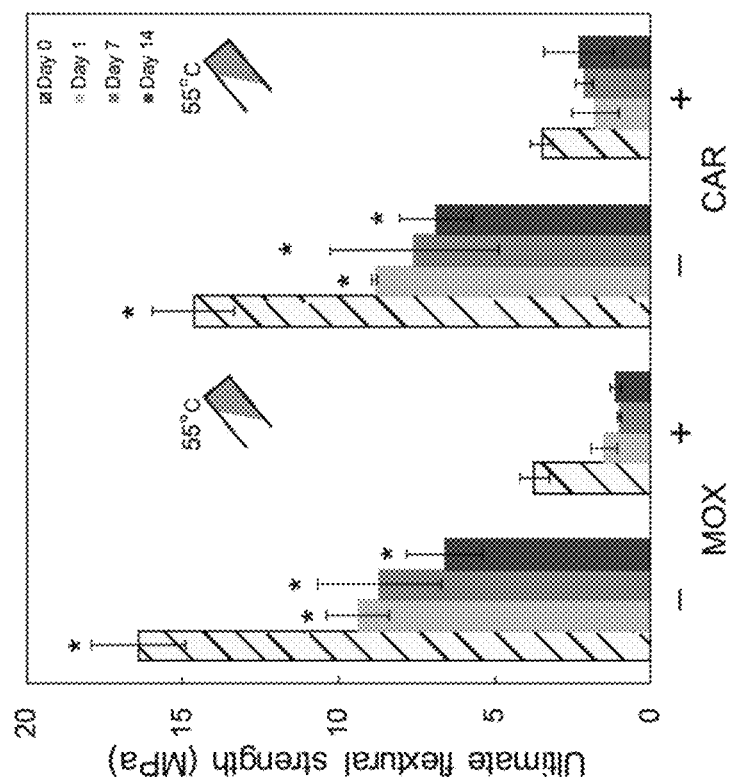
FIG. 13 is a graph of ultimate flexure strength of moxifloxacin and carbamazepine loaded arms that have been incubated in 37° C. simulated gastric fluid for times varying up to 14 days prior to and after exposure to fluid with a temperature of 55° C.

To determine the effect of gastric fluid on the bond strength between the elastomeric hinges and the drug-polymer links, a uniaxial tensile test was conducted on specimens 110 mm in length with a 2.6 mm side length square cross-section. Half the length of each specimen (55 mm) was made of thermoplastic polyurethane (Elastollan® 1185A) and the remaining half was synthesized from a given formulation for the links (e.g., PCL, moxifloxacin, carbamazepine). The two halves were joined by compression molding. To run the test, each end of the specimen was held in place using a pneumatic grip and pulled at a steady state at 1 mm/s. Similar to the three-point bending tests, the specimens were placed in 50 mL SGF for 1, 7, and 14 days and left in a 37° C. incubator shaker at 100 RPM. The tensile test was then conducted for each time point as well as a day 0 control. The effect of temperature was also investigated with an additional set of specimens that were submerged in 55° C. water for 20 sec before starting the test. Interestingly, a significant reduction in ultimate flexural strength (8 to 1.5 MPa) and ultimate flexural strain (0.06 to 0.02) on average over 14 days was observed when triggered with 55° C. water, see FIGS. 13 and 14 which show comparisons of the ultimate flexural strength and strain of MOX and CAR samples prior to and after exposure to 55° C. water after different amounts of time in simulated gastric fluid. These data, and the in vivo testing detailed above, confirm the mechanical stability and thermally activated weakening of the drug-loaded links.

Example: Experimental Summary

As detailed above, moxifloxacin and carbamazepine formulations were selected for extended drug-release and mechanical strength and flexibility to manufacture residence devices with the capacity to carry about 3 g of drugs while providing a 215 mg daily dose over two weeks. Remarkably, the optimal formulations exhibited approximately linear release of the loaded drugs up to 25% of the drug load over 14 days, as well as an ultimate flexural strength of greater than 8 MPa and an ultimate flexural strain of greater than 0.08 even after 14 days of incubation in simulated gastric fluid at 37° C. Radiograph and endoscopic evaluation of the gastric residence of the residence devices revealed that the residence devices deployed in the stomach, adopted a semispherical shape, and were notably retained for two weeks without any fracture or disassembly. Further, no evidence of gastrointestinal obstruction, ulceration or injury was observed.

While the present teachings have been described in conjunction with various embodiments and examples, it is not intended that the present teachings be limited to such embodiments or examples. On the contrary, the present teachings encompass various alternatives, modifications, and equivalents, as will be appreciated by those of skill in the art. Accordingly, the foregoing description and drawings are by way of example only.

What is claimed is:

1. A residence device comprising:
    a plurality of links, wherein at least a portion of the plurality of links include:
        a first link segment;
        a second link segment; and
        a coupling that selectively connects the first link segment to the second link segment, and wherein the coupling is configured to weaken or decouple a connection between the first link segment and the second link segment when exposed to a temperature greater than a threshold temperature; and
    a plurality of flexible hinges, wherein each hinge pivotably connects at least two links of the plurality of links to form a flexible structure such that the residence device is reconfigurable from a first contracted configuration to a second expanded configuration, wherein the residence device is configured to be retained in a stomach of a subject in the second expanded configuration, and wherein the threshold temperature is greater than normothermia of the stomach.

2. The residence device of claim 1, wherein the plurality of links include a therapeutic compound.

3. The residence device of claim 2, wherein the plurality of links are configured to release the therapeutic compound in vivo at a rate between or equal to 100 mg/day and 400 mg/day.

4. The residence device of claim 2, wherein the plurality links include an amount of the therapeutic compound between or equal to 1 g and 5 g.

5. The residence device of claim 1, further comprising a sensor attached to a portion of the residence device.

6. The residence device of claim 1, wherein the plurality of links form a three-dimensional structure in the second expanded configuration.

7. The residence device of claim 6, wherein the plurality of links form a cylindrical structure in the first contracted configuration.

8. The residence device of claim 1, wherein a minimum dimension of the residence device in the contracted configuration is less than 18 mm and a minimum dimension of the residence device in the expanded configuration is greater than 20 mm.

9. The residence device of claim 1, wherein the residence device is configured to disassemble into fragments with a maximum dimension less than or equal to 2 cm when the couplings are exposed to a temperature greater than the threshold temperature.

10. A method of using a residence device, the method comprising:
    introducing a residence device in a first contracted configuration into a stomach of a subject;
    reconfiguring the residence device into a second expanded configuration once the residence device is located in the stomach; and
    exposing the residence device to a temperature greater than a threshold temperature to selectively weaken or disassemble at least a portion of the residence device, wherein exposing the residence device to a temperature greater than a threshold temperature includes exposing the residence device to a temperature greater than normothermia of the stomach.

11. The method of claim 10, further comprising releasing a therapeutic compound from the residence device while the residence device is located in the stomach.

12. The method of claim 11, wherein releasing the therapeutic compound includes releasing the therapeutic compound at a rate between or equal to 100 mg/day and 400 mg/day.

13. The method of claim 11, wherein releasing the therapeutic compound includes releasing an amount of the therapeutic compound between or equal to 1 g and 5 g while the residence device is located in the stomach.

14. The method of claim 10, further comprising sensing one or more parameters with the residence device while the residence device is located in the stomach.

15. The method of claim 10, further comprising deploying the residence device into the stomach through an esophagus of the subject.

16. The method of claim 10, further comprising passing fragments of the residence device through a pylorus of the subject to remove the residence device from the stomach.

17. A residence device, the device comprising:
   a plurality of links;
   a plurality of flexible hinges, each hinge configured to pivotably connect at least two links of the plurality of links to form a flexible structure such that the residence device is reconfigurable from a first contracted configuration to a second expanded configuration; and
   two or more dissolvable capsules, wherein a first portion of the residence device is disposed in a first dissolvable capsule, a second portion of the residence device is disposed in a second dissolvable capsule, followed by any number of portions disposed in a subsequent capsule, and a resultant portion of the residence device extending between the dissolvable capsules, and wherein when the first and second dissolvable capsules dissolve, the residence device expands from the first contracted configuration to the second expanded configuration.

18. The residence device of claim 17, wherein the plurality of links form a three-dimensional structure in the second expanded configuration.

19. The residence device of claim 18, wherein the plurality of links form a cylindrical structure in the first contracted configuration.

20. The residence device of claim 19, wherein a minimum dimension of the residence device in the contracted configuration is less than 18 mm and a minimum dimension of the residence device in the expanded configuration is greater than 20 mm.

21. The residence device of claim 17, wherein at least a portion of the plurality of links include:
   a first link segment;
   a second link segment; and
   a coupling that selectively connects the first link segment to the second link segment, and wherein the coupling is configured to weaken or decouple a connection between the first link segment and the second link segment when exposed to a temperature greater than a threshold temperature.

22. The residence device of claim 1, wherein the threshold temperature is greater than or equal to 45 degrees Celsius.

23. The method of claim 10, wherein the threshold temperature is greater than or equal to 45 degrees Celsius.

* * * * *

UNITED STATES PATENT AND TRADEMARK OFFICE
CERTIFICATE OF CORRECTION

PATENT NO. : 11,648,381 B2
APPLICATION NO. : 16/684638
DATED : May 16, 2023
INVENTOR(S) : Robert S. Langer et al.

It is certified that error appears in the above-identified patent and that said Letters Patent is hereby corrected as shown below:

On the Title Page

At item (72), Inventors:
"Sahab I Babaee" should be replaced with: --Sahab Babaee--.
"Jiuyun | Shi" should be replaced with: --Jiuyun Shi--.

Signed and Sealed this
Twenty-fourth Day of October, 2023

Katherine Kelly Vidal
*Director of the United States Patent and Trademark Office*